(12) United States Patent
Andreiux (10) Patent No.: US 8,800,557 B2
(45) Date of Patent: Aug. 12, 2014

(54) SYSTEM AND PROCESS FOR SUPPLYING RESPIRATORY GAS UNDER PRESSURE OR VOLUMETRICALLY

(75) Inventor: Claude Andreiux, Bordes (FR)

(73) Assignee: Covidien LP, Mansfield, MA (US)

( * ) Notice: Subject to any disclaimer, the term of this patent is extended or adjusted under 35 U.S.C. 154(b) by 585 days.

(21) Appl. No.: 12/752,501

(22) Filed: Apr. 1, 2010

(65) Prior Publication Data

US 2010/0186744 A1 Jul. 29, 2010

Related U.S. Application Data

(63) Continuation of application No. 11/781,013, filed on Jul. 20, 2007, now Pat. No. 7,717,113, which is a continuation of application No. 10/899,022, filed on Jul. 27, 2004, now abandoned.

(30) Foreign Application Priority Data

Jul. 29, 2003 (FR) .................................. 03 09347

(51) Int. Cl.
*A61M 16/20* (2006.01)
*A61M 16/00* (2006.01)

(52) U.S. Cl.
USPC ............ 128/204.23; 128/200.24; 128/204.18; 128/204.21

(58) Field of Classification Search
CPC ... A61M 16/00; A61M 16/20; A61M 16/208; A61M 2016/00; A61M 2016/20; A61M 2016/208
USPC ............. 128/200.24, 204.18, 204.21, 204.23, 128/204.26
See application file for complete search history.

(56) References Cited

U.S. PATENT DOCUMENTS

| | | | |
|---|---|---|---|
| 3,444,857 A | 5/1969 | Godel | |
| 3,481,333 A | 12/1969 | Garrison | |
| 3,485,243 A | 12/1969 | Bird et al. | |
| 3,688,794 A | 9/1972 | Bird et al. | |
| 4,241,756 A | 12/1980 | Bennett et al. | |

(Continued)

FOREIGN PATENT DOCUMENTS

| | | | | |
|---|---|---|---|---|
| DE | 19714644 A | 10/1998 | ............ | A61M 16/10 |
| EP | 0862922 A | 9/1998 | ............ | A61M 16/00 |

(Continued)

OTHER PUBLICATIONS

French Search Report, FR 0309347, 4 pages.

(Continued)

*Primary Examiner* — Annette Dixon (57) ABSTRACT

The object of the invention is a device for supplying respiratory gas to a patient according to respiratory cycles, comprising a gaseous flow rate generator provided with a turbine with low inertia and high nominal speed, a first circuit called a supply circuit for the gaseous flow toward a respiratory mask or an intubation means of the patient, means for measuring pressure and/or measuring flow rate of the gaseous flow, computation means for parameters of pressure and/or flow rate, and means for controlling the speed of rotation of the generator, characterized in that the measuring means, the computation means and the speed control means coact automatically to control the speed of rotation of the turbine as a function of the inspiration and expiration phases and as a function of patient pressure signals and/or inspiration flow rate signals.

19 Claims, 1 Drawing Sheet

(56) References Cited

U.S. PATENT DOCUMENTS

| | | | |
|---|---|---|---|
| 4,481,944 A * | 11/1984 | Bunnell ................... 128/204.18 |
| 4,527,557 A | 7/1985 | DeVries et al. |
| 4,608,976 A | 9/1986 | Suchy |
| 4,699,137 A | 10/1987 | Schroeder |
| RE32,553 E | 12/1987 | Bennett et al. |
| 4,712,580 A | 12/1987 | Gilman et al. |
| 4,727,871 A | 3/1988 | Smargiassi et al. |
| 4,747,403 A | 5/1988 | Gluck et al. |
| 4,752,089 A | 6/1988 | Carter |
| 4,921,642 A | 5/1990 | LaTorraca |
| 4,954,799 A | 9/1990 | Kumar |
| 4,957,107 A | 9/1990 | Sipin |
| 4,991,576 A | 2/1991 | Henkin et al. |
| 4,993,269 A | 2/1991 | Guillaume et al. |
| 5,000,173 A | 3/1991 | Zalkin et al. |
| 5,020,532 A | 6/1991 | Mahoney et al. |
| 5,057,822 A | 10/1991 | Hoffman |
| 5,072,729 A | 12/1991 | DeVries |
| 5,072,737 A | 12/1991 | Goulding |
| 5,107,830 A * | 4/1992 | Younes ................... 128/204.18 |
| 5,109,838 A | 5/1992 | Elam |
| 5,127,400 A | 7/1992 | DeVries et al. |
| 5,134,995 A | 8/1992 | Gruenke et al. |
| 5,150,291 A | 9/1992 | Cummings et al. |
| 5,161,525 A | 11/1992 | Kimm et al. |
| 5,168,868 A | 12/1992 | Hicks |
| 5,178,155 A | 1/1993 | Mault |
| 5,237,987 A * | 8/1993 | Anderson et al. ........ 128/204.18 |
| 5,255,675 A | 10/1993 | Kolobow |
| 5,259,373 A | 11/1993 | Gruenke et al. |
| 5,269,293 A | 12/1993 | Loser et al. |
| 5,271,389 A | 12/1993 | Isaza et al. |
| 5,277,175 A | 1/1994 | Riggs et al. |
| 5,279,549 A | 1/1994 | Ranford |
| 5,299,568 A | 4/1994 | Forare et al. |
| 5,301,667 A | 4/1994 | McGrail et al. |
| 5,301,921 A | 4/1994 | Kumar |
| 5,303,699 A | 4/1994 | Bonassa et al. |
| 5,309,901 A | 5/1994 | Beaussant |
| 5,319,540 A | 6/1994 | Isaza et al. |
| 5,325,861 A | 7/1994 | Goulding |
| 5,331,995 A | 7/1994 | Westfall et al. |
| 5,333,606 A | 8/1994 | Schneider et al. |
| 5,339,807 A | 8/1994 | Carter |
| 5,343,857 A | 9/1994 | Schneider et al. |
| 5,343,858 A | 9/1994 | Winefordner et al. |
| 5,351,522 A | 10/1994 | Lura |
| 5,357,946 A | 10/1994 | Kee et al. |
| 5,360,000 A | 11/1994 | Carter |
| 5,368,019 A | 11/1994 | LaTorraca |
| 5,368,021 A | 11/1994 | Beard et al. |
| 5,383,449 A | 1/1995 | Forare et al. ............. 128/205.11 |
| 5,385,142 A | 1/1995 | Brady et al. |
| 5,390,666 A | 2/1995 | Kimm et al. |
| 5,398,677 A | 3/1995 | Smith |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,452,714 A * | 9/1995 | Anderson et al. ........ 128/205.11 |
| 5,467,766 A | 11/1995 | Ansite et al. |
| 5,484,270 A | 1/1996 | Adahan |
| 5,494,028 A | 2/1996 | DeVries et al. |
| 5,497,767 A | 3/1996 | Olsson et al. |
| 5,503,140 A | 4/1996 | Winefordner et al. |
| 5,503,146 A | 4/1996 | Froehlich et al. ........ 128/204.23 |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. ............... 128/204.23 |
| 5,540,220 A | 7/1996 | Gropper et al. .......... 128/204.23 |
| 5,542,415 A | 8/1996 | Brody |
| 5,542,416 A | 8/1996 | Chalvignac |
| 5,544,674 A | 8/1996 | Kelly |
| 5,546,933 A | 8/1996 | Rapoport et al. ........ 128/204.23 |
| 5,546,935 A | 8/1996 | Champeau |
| 5,549,106 A | 8/1996 | Gruenke et al. |
| 5,551,419 A | 9/1996 | Forehlich et al. ........ 128/204.23 |
| 5,568,910 A | 10/1996 | Koehler et al. |
| 5,575,283 A | 11/1996 | Sjoestrand |
| 5,596,984 A | 1/1997 | O'Mahony et al. |
| 5,606,968 A | 3/1997 | Mang |
| 5,617,847 A | 4/1997 | Howe |
| 5,630,411 A | 5/1997 | Holscher |
| 5,632,270 A | 5/1997 | O'Mahony et al. |
| 5,645,048 A | 7/1997 | Brodsky et al. |
| 5,647,355 A * | 7/1997 | Starr et al. ............... 128/205.24 |
| 5,657,750 A | 8/1997 | Colman et al. |
| 5,660,171 A | 8/1997 | Kimm et al. |
| 5,662,099 A | 9/1997 | Tobia et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,678,537 A | 10/1997 | Bathe et al. |
| 5,683,232 A | 11/1997 | Adahan |
| 5,692,497 A | 12/1997 | Schnitzer et al. |
| 5,697,363 A | 12/1997 | Hart |
| 5,701,883 A | 12/1997 | Hete et al. |
| 5,701,889 A | 12/1997 | Danon |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,614 A | 8/1998 | Gruenke et al. |
| 5,794,986 A | 8/1998 | Gansel et al. |
| 5,797,393 A | 8/1998 | Kohl |
| 5,803,064 A | 9/1998 | Phelps et al. |
| 5,813,399 A | 9/1998 | Isaza et al. |
| 5,823,179 A | 10/1998 | Grychowski et al. |
| 5,826,575 A | 10/1998 | Lall |
| 5,829,441 A | 11/1998 | Kidd et al. |
| 5,845,636 A | 12/1998 | Gruenke et al. |
| 5,857,458 A | 1/1999 | Tham et al. |
| 5,864,938 A | 2/1999 | Gansel et al. |
| 5,865,168 A | 2/1999 | Isaza |
| 5,868,133 A | 2/1999 | DeVries et al. |
| 5,875,783 A | 3/1999 | Kullik ...................... 128/204.18 |
| 5,876,352 A | 3/1999 | Weismann |
| 5,881,717 A | 3/1999 | Isaza |
| 5,881,722 A | 3/1999 | DeVries et al. |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,934,274 A | 8/1999 | Merrick et al. |
| 5,937,856 A | 8/1999 | Jonasson et al. |
| 5,941,846 A | 8/1999 | Duffy et al. |
| 5,957,130 A | 9/1999 | Krahbichler et al. |
| 6,024,089 A | 2/2000 | Wallace et al. |
| 6,041,777 A | 3/2000 | Faithfull et al. |
| 6,041,780 A | 3/2000 | Richard et al. |
| 6,047,860 A | 4/2000 | Sanders |
| 6,073,630 A | 6/2000 | Adahan |
| 6,076,523 A | 6/2000 | Jones et al. |
| 6,095,139 A | 8/2000 | Psaros ...................... 128/204.22 |
| 6,102,038 A | 8/2000 | DeVries |
| 6,116,240 A | 9/2000 | Merrick et al. |
| 6,116,242 A | 9/2000 | Frye et al. |
| 6,116,464 A | 9/2000 | Sanders |
| 6,119,686 A | 9/2000 | Somerson et al. |
| 6,123,073 A | 9/2000 | Schlawin et al. |
| 6,123,074 A | 9/2000 | Hete et al. |
| 6,131,571 A | 10/2000 | Lampotang et al. ..... 128/204.21 |
| 6,135,106 A | 10/2000 | Dirks et al. |

(56) References Cited

U.S. PATENT DOCUMENTS

| | | | |
|---|---|---|---|
| 6,135,967 A | 10/2000 | Fiorenza et al. | |
| 6,142,150 A | 11/2000 | O'Mahoney et al. | |
| 6,148,814 A | 11/2000 | Clemmer et al. | |
| 6,152,132 A | 11/2000 | Psaros | 128/204.25 |
| 6,152,135 A | 11/2000 | DeVries et al. | |
| 6,158,432 A | 12/2000 | Biondi et al. | |
| 6,161,539 A | 12/2000 | Winter | |
| 6,176,234 B1 | 1/2001 | Salter et al. | |
| 6,192,885 B1 | 2/2001 | Jalde | |
| 6,217,524 B1 | 4/2001 | Orr et al. | |
| 6,220,245 B1 | 4/2001 | Takabayashi et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,287,264 B1 | 9/2001 | Hoffman | |
| 6,295,330 B1 | 9/2001 | Skog et al. | |
| 6,295,985 B1 | 10/2001 | Kock et al. | |
| 6,305,373 B1 | 10/2001 | Wallace et al. | |
| 6,306,098 B1 | 10/2001 | Orr et al. | |
| 6,308,706 B1 | 10/2001 | Lammers et al. | |
| 6,309,360 B1 | 10/2001 | Mault | |
| 6,321,748 B1 | 11/2001 | O'Mahoney | |
| 6,325,785 B1 | 12/2001 | Babkes et al. | |
| 6,349,922 B1 | 2/2002 | Rydin | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,371,113 B1 | 4/2002 | Tobia et al. | |
| 6,412,483 B1 | 7/2002 | Jones et al. | |
| 6,415,788 B1 | 7/2002 | Clawson et al. | |
| 6,419,634 B1 | 7/2002 | Gaston, IV et al. | |
| 6,439,229 B1 | 8/2002 | Du et al. | |
| 6,457,472 B1 | 10/2002 | Schwartz et al. | |
| 6,467,478 B1 | 10/2002 | Merrick et al. | |
| 6,523,537 B1 | 2/2003 | Mas Marfany | |
| 6,523,538 B1 | 2/2003 | Wikefeldt | |
| 6,526,970 B2 | 3/2003 | DeVries et al. | |
| 6,543,449 B1 | 4/2003 | Woodring et al. | 128/204.18 |
| 6,546,930 B1 | 4/2003 | Emerson et al. | |
| 6,550,479 B1 | 4/2003 | Duxbury | |
| 6,553,991 B1 | 4/2003 | Isaza | |
| 6,557,553 B1 | 5/2003 | Borrello | |
| 6,557,554 B1 | 5/2003 | Sugiura | |
| 6,564,798 B1 | 5/2003 | Jalde | |
| 6,571,795 B2 | 6/2003 | Bourdon | |
| 6,572,561 B2 | 6/2003 | Mault | |
| 6,575,164 B1 | 6/2003 | Jaffe et al. | |
| 6,575,165 B1 | 6/2003 | Cook et al. | |
| 6,575,918 B2 | 6/2003 | Kline | |
| 6,584,973 B1 | 7/2003 | Biondi et al. | |
| 6,606,994 B1 | 8/2003 | Clark | |
| 6,616,615 B2 | 9/2003 | Mault | |
| 6,619,289 B1 | 9/2003 | Mashak | |
| 6,622,725 B1 | 9/2003 | Fisher et al. | |
| 6,622,726 B1 | 9/2003 | Du | |
| 6,626,175 B2 | 9/2003 | Jafari et al. | 128/204.21 |
| 6,629,934 B2 | 10/2003 | Mault et al. | |
| 6,631,716 B1 | 10/2003 | Robinson et al. | |
| 6,644,310 B1 | 11/2003 | Delache et al. | |
| 6,668,824 B1 | 12/2003 | Isaza et al. | |
| 6,675,801 B2 | 1/2004 | Wallace et al. | |
| 6,718,974 B1 | 4/2004 | Moberg | |
| 6,722,359 B2* | 4/2004 | Chalvignac | 128/204.18 |
| 6,723,055 B2 | 4/2004 | Hoffman | |
| 6,725,447 B1 | 4/2004 | Gilman et al. | |
| 6,729,331 B2 | 5/2004 | Kay | |
| 6,739,334 B2 | 5/2004 | Valeij | |
| 6,739,337 B2 | 5/2004 | Isaza | |
| 6,761,167 B1 | 7/2004 | Nadjafizadeh et al. | |
| 6,761,168 B1 | 7/2004 | Nadjafizadeh et al. | |
| 6,763,829 B2 | 7/2004 | Jaffe et al. | |
| 6,772,762 B2 | 8/2004 | Piesinger | |
| 6,805,121 B1 | 10/2004 | Flood et al. | |
| 6,814,074 B1 | 11/2004 | Nadjafizadeh et al. | |
| 6,866,040 B1 | 3/2005 | Bourdon | |
| 6,877,511 B2 | 4/2005 | DeVries et al. | 128/204.26 |
| 6,886,558 B2 | 5/2005 | Tanaka | |
| 6,896,713 B1 | 5/2005 | Eckerbom et al. | |
| 6,938,619 B1 | 9/2005 | Hickle | |
| 6,960,854 B2 | 11/2005 | Nadjafizadeh et al. | |
| 6,968,840 B2 | 11/2005 | Smith et al. | |
| 7,032,589 B2 | 4/2006 | Kerechanin, II et al. | |
| 7,036,504 B2 | 5/2006 | Wallace et al. | |
| 7,040,315 B1 | 5/2006 | Strömberg | |
| 7,040,321 B2 | 5/2006 | Göbel | |
| 7,043,979 B2 | 5/2006 | Smith et al. | |
| 7,066,175 B2 | 6/2006 | Hamilton et al. | |
| 7,066,177 B2 | 6/2006 | Pittaway et al. | |
| 7,077,131 B2 | 7/2006 | Hansen | |
| RE39,225 E | 8/2006 | Isaza et al. | |
| 7,117,438 B2 | 10/2006 | Wallace et al. | |
| 7,118,537 B2 | 10/2006 | Baddour | |
| 7,121,277 B2 | 10/2006 | Ström | |
| 7,152,604 B2 | 12/2006 | Hickle et al. | |
| 7,168,597 B1 | 1/2007 | Jones et al. | |
| 7,195,013 B2 | 3/2007 | Lurie | |
| 7,210,478 B2 | 5/2007 | Banner et al. | |
| 7,222,623 B2 | 5/2007 | DeVries et al. | |
| 7,241,269 B2 | 7/2007 | McCawley et al. | |
| 7,270,126 B2 | 9/2007 | Wallace et al. | |
| 7,275,540 B2 | 10/2007 | Bolam et al. | |
| 7,291,115 B2 | 11/2007 | Cardona Burrul | |
| 7,302,949 B2 | 12/2007 | Pelerossi et al. | |
| 7,320,321 B2 | 1/2008 | Pranger et al. | |
| 7,347,825 B2 | 3/2008 | Vaughan et al. | |
| 7,369,757 B2 | 5/2008 | Farbarik | |
| 7,370,650 B2 | 5/2008 | Nadjafizadeh et al. | |
| 7,392,806 B2 | 7/2008 | Yuen et al. | |
| 7,428,902 B2 | 9/2008 | Du et al. | |
| 7,460,959 B2 | 12/2008 | Jafari | |
| 7,475,685 B2 | 1/2009 | Dietz et al. | |
| 7,484,508 B2 | 2/2009 | Younes | |
| 7,487,773 B2 | 2/2009 | Li | |
| 7,487,778 B2 | 2/2009 | Freitag | |
| 7,500,483 B2 | 3/2009 | Colman et al. | |
| 7,509,957 B2 | 3/2009 | Duquette et al. | |
| 7,525,663 B2 | 4/2009 | Kwok et al. | |
| 7,533,670 B1 | 5/2009 | Freitag et al. | |
| 7,547,285 B2 | 6/2009 | Kline | |
| 7,556,038 B2 | 7/2009 | Kirby et al. | |
| 7,556,042 B2 | 7/2009 | West et al. | |
| 7,562,657 B2 | 7/2009 | Blanch et al. | |
| 7,588,033 B2 | 9/2009 | Wondka | |
| 7,610,914 B2 | 11/2009 | Bolam et al. | |
| 7,617,824 B2 | 11/2009 | Doyle | |
| 7,621,271 B2 | 11/2009 | Brugnoli | |
| 7,634,998 B1 | 12/2009 | Fenley | |
| 7,654,802 B2 | 2/2010 | Crawford, Jr. et al. | |
| 7,686,019 B2 | 3/2010 | Weiss | |
| 7,694,677 B2 | 4/2010 | Tang | |
| 7,699,788 B2 | 4/2010 | Kuck et al. | |
| 7,717,113 B2* | 5/2010 | Andrieux | 128/204.23 |
| 7,721,735 B2 | 5/2010 | Hamilton et al. | |
| 7,721,736 B2 | 5/2010 | Urias et al. | |
| D618,356 S | 6/2010 | Ross | |
| 7,740,591 B1 | 6/2010 | Starr et al. | |
| 7,753,052 B2 | 7/2010 | Tanaka | |
| 7,779,840 B2 | 8/2010 | Acker et al. | |
| 7,784,461 B2 | 8/2010 | Figueiredo et al. | |
| 7,810,497 B2 | 10/2010 | Pittman et al. | |
| 7,814,908 B2 | 10/2010 | Psaros | |
| 7,819,815 B2 | 10/2010 | Younes | |
| 7,823,588 B2 | 11/2010 | Hansen | |
| 7,828,741 B2 | 11/2010 | Kline et al. | |
| 7,846,739 B2 | 12/2010 | von Bahr et al. | |
| 7,849,854 B2 | 12/2010 | DeVries et al. | |
| 7,855,716 B2 | 12/2010 | McCreary et al. | |
| 7,861,716 B2 | 1/2011 | Borrello | |
| 7,870,857 B2 | 1/2011 | Dhuper et al. | |
| D632,796 S | 2/2011 | Ross et al. | |
| D632,797 S | 2/2011 | Ross et al. | |
| 7,883,471 B2 | 2/2011 | Aljuri et al. | |
| 7,885,771 B2 | 2/2011 | Roecker et al. | |
| 7,891,354 B2 | 2/2011 | Farbarik | |

(56) References Cited

U.S. PATENT DOCUMENTS

| | | |
|---|---|---|
| 7,893,560 B2 | 2/2011 | Carter |
| 7,900,626 B2 | 3/2011 | Daly |
| 7,913,690 B2 | 3/2011 | Fisher et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| D649,157 S | 11/2011 | Skidmore et al. |
| 8,113,062 B2 | 2/2012 | Graboi et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0005197 A1 | 1/2002 | DeVries et al. .......... 128/204.21 |
| 2002/0014239 A1 | 2/2002 | Chalvignac ............. 128/204.18 |
| 2002/0026941 A1 | 3/2002 | Biondi et al. |
| 2002/0053345 A1* | 5/2002 | Jafari et al. ............. 128/204.23 |
| 2002/0138213 A1 | 9/2002 | Mault |
| 2003/0062045 A1 | 4/2003 | Woodring et al. |
| 2004/0138577 A1 | 7/2004 | Kline |
| 2004/0261793 A1 | 12/2004 | Stromberg et al. |
| 2005/0039748 A1 | 2/2005 | Andrieux |
| 2005/0098177 A1 | 5/2005 | Haj-Yahya et al. |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0217671 A1 | 10/2005 | Fisher et al. |
| 2006/0032499 A1 | 2/2006 | Halsnes |
| 2006/0129054 A1 | 6/2006 | Orr et al. |
| 2006/0130839 A1 | 6/2006 | Bassovitch |
| 2006/0201507 A1 | 9/2006 | Breen |
| 2006/0249148 A1 | 11/2006 | Younes |
| 2006/0249153 A1 | 11/2006 | DeVries et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0062531 A1 | 3/2007 | Fisher et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0113854 A1 | 5/2007 | Mcauliffe |
| 2007/0125377 A1 | 6/2007 | Heinonen et al. |
| 2007/0144521 A1 | 6/2007 | DeVries et al. |
| 2007/0144523 A1 | 6/2007 | Bolam et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0227537 A1 | 10/2007 | Bemister et al. |
| 2007/0232952 A1 | 10/2007 | Baddour |
| 2007/0255160 A1 | 11/2007 | Daly |
| 2007/0284361 A1 | 12/2007 | Nadjafizadeh et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0135044 A1 | 6/2008 | Freitag et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman, Jr. |
| 2009/0071478 A1 | 3/2009 | Kalfon |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlmén et al. |
| 2009/0293877 A1 | 12/2009 | Blanch et al. |
| 2009/0299430 A1 | 12/2009 | Davies et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |

(56) References Cited

U.S. PATENT DOCUMENTS

| | | |
|---|---|---|
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0242961 A1 | 9/2010 | Mougel et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0282258 A1 | 11/2010 | Tailor et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300446 A1 | 12/2010 | Nicolazzi et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0011400 A1 | 1/2011 | Gentner et al. |
| 2011/0023879 A1 | 2/2011 | Vandine et al. |
| 2011/0041849 A1 | 2/2011 | Chen et al. |
| 2011/0041850 A1 | 2/2011 | Vandine et al. |
| 2011/0066060 A1 | 3/2011 | von Bahr et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0175728 A1 | 7/2011 | Baker, Jr. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |

FOREIGN PATENT DOCUMENTS

| | | | |
|---|---|---|---|
| EP | 1243282 A | 9/2002 | A61M 16/00 |
| FR | 2663547 A1 | 12/1991 | A61M 16/00 |
| FR | 2822384 A1 | 9/2002 | A61M 16/00 |
| GB | 2324122 A | 5/2000 | F04D 29/30 |
| WO | 00/24447 | 5/2000 | A61M 16/00 |
| WO | 02/26305 | 4/2002 | A61M 16/00 |
| WO | WO 2007/102866 | 9/2007 | |

OTHER PUBLICATIONS

7200 Series Ventilator, Options, and Accessories: Operators Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

* cited by examiner

SYSTEM AND PROCESS FOR SUPPLYING RESPIRATORY GAS UNDER PRESSURE OR VOLUMETRICALLY

RELATED APPLICATION

This application is a continuation of U.S. patent application Ser. No. 11/781,013 filed Jul. 20, 2007, and issued as U.S. Pat. No. 7,717,113, which is a continuation application of U.S. patent application Ser. No. 10/899,022, filed on Jul. 27, 2004, which was abandoned, which claims priority to French Application No. 03 09347 filed Jul. 29, 2003, the contents of which are hereby incorporated by reference in their entirety.

TECHNICAL FIELD

The present invention relates to a device and process for supplying respiratory gas.

BACKGROUND

Devices for supplying respiratory gas are used particularly in the treatment of respiratory ailments of adult or infant patients.

Such devices are adapted to supply a quantity of air, if desired with added oxygen, either in the form of a quantified breathable volume, or in the form of a first predetermined pressure called inspiration pressure and a second predetermined pressure called expiration pressure.

WO 00/24447 relates to a device for supplying respiratory gas provided with a compressor delivering a flow of gas under pressure to a patient through a downstream accumulator/silencer and a flow rate regulating valve. According to this document, the surplus of unneeded gas is returned to an upstream filter/accumulator through a bypass valve so as to limit the loss of respiratory gas.

FR 2 663 547 A1 relates to apparatus for continuously providing an overpressure of respiratory gas; this apparatus using a high speed turbine supplying gas under constant predetermined pressure regulated by measuring the pressure at the respiratory mask of the patient. This apparatus is passive in that the pressure is maintained continuously, the expiration phases being possible thanks to a calibrated loss at the respiratory mask of the patient.

FR 2 822 384 A1 in the name of the applicant relates to a mixed pulmonary ventilator provided with a flow generator, the circulation means permitting re-injecting the flow upstream of the generator during an expiration phase of the patient, the circulation means comprising particularly a regulating valve comprising two flaps actuated by the same actuator permitting several modes of regulation and an optimization of the flow as a function of the inspiration and expiration phases. According to this document, the speed of rotation of the generator is maintained constant, the pressure in the patient circuit being controlled by the two flaps which permit return of the gas to the generator particularly during the expiration phases.

SUMMARY

It remains that the circuits and systems necessary to provide and to regulate levels of pressure and/or volumetric quantities of respiratory gas are complicated and cumbersome with the control of the flaps and valves being sensitive.

The present invention seeks to provide an improved device for supplying respiratory gas which automatically controls the turbine for inspiration and expiration phases and does not use a return system for gas upstream of the turbine, thereby simplifying the system, whilst permitting operation with a sealed circuit at the respiratory mask or of the intubation device of the patient during inspiration phases and loss during expiration phases.

To this end, the present invention relates to a device for supplying respiratory gas to a patient according to respiratory cycles comprising a gas for a generator, a circuit for bringing the gaseous flow to a respiratory mask or intubation device of the patient, means for measuring the pressure and/or for measuring the gaseous flow rate, means for computing the parameters of pressure and/or flow rate, and control means of the speed of rotation of the generator, in which device the measuring means act on the speed control means through computer means to automatically control the speed of rotation of the turbine as a function of inspiration and expiration phases as a function of patient pressure signals and/or inspiration flow rate signals.

The pressure measuring means may, in particular, comprise a patient pressure sensor and/or an expiration valve pressure sensor.

The flow rate measuring means may, in particular, comprise an inspiration flow rate sensor disposed adjacent the outlet of the generator.

The flow rate measuring means may comprise an expiration flow rate sensor in a patient return circuit.

In a particular embodiment, the device may comprise a passive member for generating a pressure drop in the supply circuit. This passive member may, in particular, be a non-return flap, if desired associated with a passive flap for admission of external air downstream of the non-return flap in the supply circuit.

According to a particular embodiment of the invention, the device comprises an expiration circuit provided with an expiration valve and a proportional electro-valve for controlling said expiration valve by application of a counter-pressure.

The invention relates moreover to a process for providing a respiratory gas according to respiratory cycles, comprising inspiration and expiration phases, according to which said measurement means and said computing means act on said speed control means to automatically control the speed of rotation of the turbine as a function of the pressure and/or volume standards, of the detection of the inspiration and expiration phases, of patient pressure signals and/or inspiration flow rate signals, the supply of the respiratory gas taking place as to pressure or as to volume.

The process may preferably comprise phases of pressure increase with pressure increase slopes effected by acceleration of the turbine.

More particularly, the transition between an inspiration phase and an expiration phase can be effected by controlled deceleration of the turbine.

The process may comprise, during expiration phases, a control of an expiration valve with a pressure regulating member of the first circuit, via a proportional electro-valve which is part of a second circuit, the valve being a part of a third circuit connected to the mask or to the intubation device.

Preferably, the computing means and the control means of the speed of rotation of the generator may adapt the speed of the turbine as a function of an expiration pressure threshold beyond a regulated loss by the expiration valve so as to create a rinsing flow rate in the first circuit.

More particularly, during insufflation phases corresponding to the inspiration phases, an expiration valve, which is a part of a third circuit connected to the mask or to the intubation device, may be controlled for following the pressure through a proportional electro-valve and a second circuit.

In a particular embodiment, the process may comprise a measurement of expiration flow rate and a measurement of inspiration flow rate.

Other advantages and characteristics of the invention will become apparent from a reading of the description which follows and of a non-limiting example of the invention.

DETAILED DESCRIPTION

Figure 1:
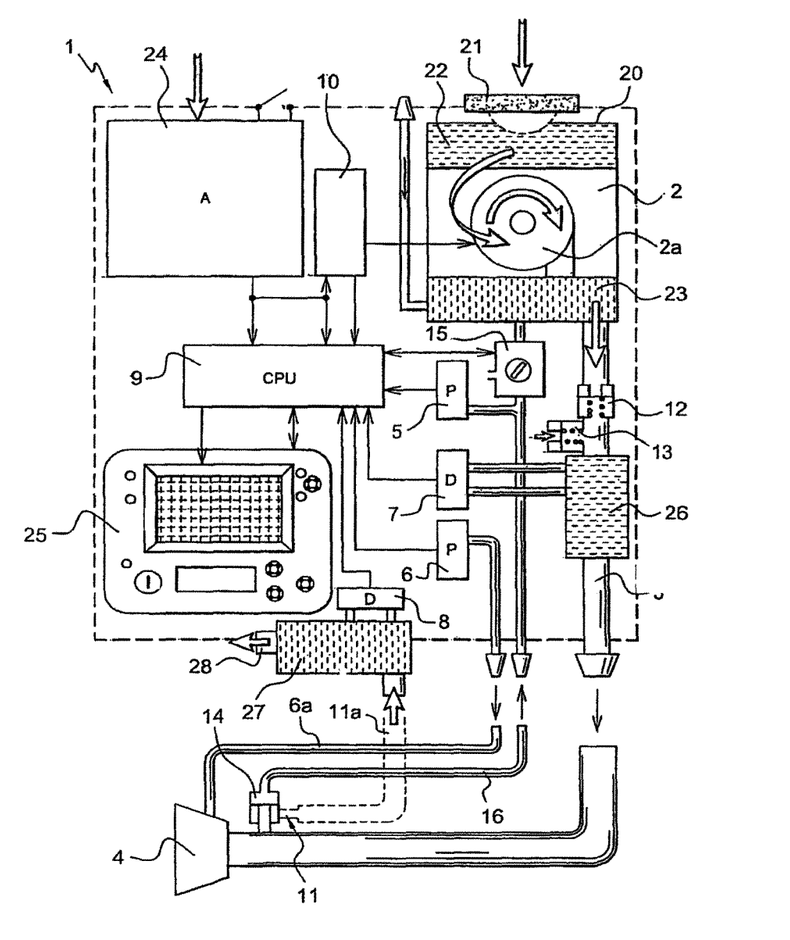
FIG. 1 is a schematic view of a device for supplying respiratory gas according to the invention.

The device 1 for supplying respiratory gas or ventilation device according to FIG. 1, comprises a generator 2 of gaseous flow provided with a turbine 2a of low inertia and high rate speed. This gaseous flow generator is disposed in a chamber 20, preceded by a filter 21 for ambient air inlet, by an upstream and downstream sound deadening means 22 and 23. The turbine 2a is for example a turbine with a maximum speed of rotation of the order of 50,000 rpm, adapted to supply a pressure of 70 millibar above ambient and a flow rate of the order of 200 l/min.

The air flow generator, thus comprises a micro-turbine with low inertia, driven by an electric motor, controlled by a computer or a computer means 9 so as to provide a wide range of flow rates and pressures.

At the outlet of the chamber 20, the generator is connected to a first circuit 3 called a circuit for supplying gaseous flow toward a respiratory mask 4 or a intubation device (not shown) of the patient.

The generator is controlled by control means 10 in the form of an electronic control card connected to a supply 24 and to computer means 9 in the form of an electronic card with a microprocessor provided with control software and connected to a control interface 25 with a screen and a keyboard.

So as to control the operation of the device and to cause it to operate, the computer means are connected to means 5, 6, 7, 8 for measuring the pressure and/or for measuring the flow rate of the gaseous flow in the form of sensors. The sensor 6 is a pressure sensor connected to a first circuit 3 which is a circuit for supplying gas to the mask 4 or intubation device of the patient.

According to the example, a sensor 6 is disposed in the apparatus 1 and connected to the mask 4 or to the intubation device via a tube 6a.

The sensor 5 is a pressure sensor connected to a second circuit 16 comprising a proportional electro-valve 15 whose operation will be described later.

The sensor 7 is an inspiration flow rate sensor disposed in the first circuit, in a laminator 26 controlling the flow of gas leaving the generator.

An expiration flow rate sensor 8, in the third circuit 11 called patient return circuit, completes the measurement means.

The computation means 9 controls the members such as the generator and the proportional electro-valve 15 as a function of standards entered into the interface 25 as a function of the ventilation programs and as a function of the pressure and/or flow rate parameters from the sensors.

According to the invention, the measuring means 5, 6, 7, 8, the computing means 9 and the speed control means 10 coact in the first instance automatically to control the speed of rotation of the turbine 2a as a function of the inspiration and expiration phases and as a function of the patient pressure signals and/or inspiration flow rate signals.

So as to regulate the output flow of the generator, the device according to FIG. 1 comprises a passive member 12 for generating a pressure drop in the supply circuit in the form of a non-return flap 12 mounted in the first circuit 3. Due to this member, the pressure on the generator side is always slightly greater than the pressure in the circuit 3 on the mask supply side or intubation device, which permits among other things a better regulation of the operation of the device.

Downstream of this non-return valve 12, the circuit 3 comprises a passive flap 13 for the admission of external air. This flap permits limiting the inspiration force of the patient by spontaneous respiration through the machine when the latter is not in operation.

On the mask side 4 of the intubation device after the circuit 3 for supplying gas, is located a third circuit 1 called an expiration circuit. This expiration circuit comprises an expiration valve 14 with a membrane permitting opening a passage either directly to the exterior or through tubing 1a toward a laminator 27 and an air outlet 28.

On the mask side 4 of the intubation device after the circuit 3 for supplying gas, is located a third circuit 11 called an expiration circuit. This expiration circuit comprises an expiration valve 14 with a membrane permitting opening a passage either directly to the exterior or through tubing 11a toward a laminator 27 and an air outlet 28.

The electro-valve permits controlling the valve 14 by applying a counter-pressure which closes the valve or limits its opening such that the expiration pressure will remain higher than the pressure of the second circuit 16. To release the valve 14, the electro-valve is controlled such that the pressure of the generator will be blocked, the second path of the free air being placed in communication with the third path.

Thus, a controlled expiration device is constructed about the expiration valve 14 controlled by the electro-valve 15 connected to the flow generator, this electro-valve 15 permitting sending a portion of the generated flow to the expiration valve so as to oppose its opening.

The proportional electro-valve 15 is controlled by control means coupled to the computation means 9 and, according to the example, disposed on the card receiving the computing means 9.

This device thus permits in operation, the control of the speed of the turbine 2a and the control of the expiration valve through the electro-valve to provide several modes of operation and particularly modes of volumetric operation. Thus, several modes of operation are sought and particularly modes of operation with inspiration and expiration pressure standards or modes for which a volume of air called a target volume is predetermined, or mixed modes.

The operation of the apparatus is based on a system of self-adaptive closed loop control of the speed of the flow generator. With this flow generator is associated a controlled expiration device, without a member for regulation of the supplemental principal flow.

In particular, the detection of an increasing slope of pressure can be translated by a level of acceleration of the turbine 2a and the detection of the transition between the inspiration phase and the expiration phase can be translated by a deceleration of the turbine 2a.

This control is effected by inspiration pressure or flow rate signals and according to control laws, based on proportional and integral coefficients, which differ according to the modes of ventilation, the adjustments of the pressure or flow rate and in particular the phases of the respiratory cycle.

The operation of the device and the associated ventilation process will be explained for example in the case of a mode in which an inspiration pressure Pi, an expiration pressure Pe, as well as a form of obtaining the inspiration pressure based on the time of pressure increase, are fixed. The time of insufflation is here dependent on a level of triggering the expiration adjusted on the basis of the measurement of a drop in flow rate measured in the inspiration detector 7, after obtaining a maximum insufflation flow rate available for the patient.

A limiting parameter for the time of insufflation is the minimum threshold corresponding to the slope of pressure measured; another parameter is a maximum threshold of safety for the insufflation time which corresponds to the last inspiration time carried out or at most to three seconds. Other safety parameters can be taken into account such as a safety frequency.

According to this embodiment, the objective of the insufflation phase is the establishment of a pressure level Pi with a variable time of increase and a holding time depending on the behavior of the associated flow rate.

The objective of the expiration phase is to maintain a pressure level Pe up to the beginning of the following inspiration phase, but also sufficiently to rinse the circuit so as to evacuate the residual expired gases.

To carry out inspiration cycles, the phases of pressure increase with increased slopes of pressure are carried out by an acceleration of the turbine 2a. The pressure is controlled in the inspiration pressure sensor 6.

During the insufflation phase corresponding to the inspiration phase, the computation means control the expiration valve 14, which is part of the third circuit 11 connected to the mask 4 or to the intubation device, via the proportional electro-valve 15 and the second circuit 16, according to pressure.

The transition between an inspiration phase and an expiration phase is effected by a controlled deceleration of the turbine 2a and the expiration valve 14, which is part of the third circuit 11 connected to the mask 4 or to the intubation device, is controlled, through the proportional electro-valve 15 and the second circuit 16, with a pressure regulation member of the first circuit 3.

During the expiration phase, the computation means and the means for controlling the speed of rotation of the generator adapt the speed of the turbine 2a as a function of an expiration pressure threshold beyond a loss regulated by the expiration valve 14 so as to create the rinsing flow rate of the first circuit.

The non-return valve 12 and the spontaneous respiration valve 13 permit balancing the rinsing pressure which is maintained sufficiently low to limit the phenomenon of expiration braking without being canceled to avoid all heating of the turbine 2a.

In the case of ventilation for which a current volume as well as a frequency and a cycling ratio are fixed, the objective of the insufflation phase is the distribution of a current volume Vt with a suitable flow rate shape and during a time fixed by the frequency levels and the ratio of cycling regulated by the interface 25.

In this case, during insufflation, the patient current comprising the circuit 3, the mask 4 or intubation device is maintained sealed, against parasitic loss by the closing of the valve 14 controlled by the electro-valve 15. As a result, there is an increase in pressure of the circuit 3 and of the pulmonary system of the patient depending on the characteristics of the patient. In the case of exceeding the objective of maximum pressure measured with the pressure sensor 6, it is possible to cause the pressure in the control circuit 16 of the valve 14 by a command of the electro-valve 15 and to pass immediately into the expiration phase.

In the case of a target volume mode, the operator enters by the interface means a target volume standard into the computation means 9 which, as a function of this parameter and other parameters entered by the interface such as the frequency of minimum cycle and/or safety, cycling ratio, high pressure threshold, will permanently adjust the insufflation pressure between a low pressure threshold and a maximum pressure threshold so as to maintain the current volume inhaled by the patient as nearly as possible to a predefined target volume, namely for example between target volume Vt and target volume Vt+20%.

According to the target volume mode, it is particularly necessary to, at the same time, precisely adjust the pressure by pressure steps between the cycles. For example, for a pressure standard of the order of 20 millibars, the steps between cycles are defined between 0.5 millibar and 2 millibars so as to react immediately to the detection of an unbalance without having a strong reaction that would be uncomfortable to the patient.

This pressure adjustment is made according to the invention without a regulator device, such as the generator, but by controlling the speed of the turbine 2a of the generator 2 as a function of the pressure measurements of the sensor 6 of the pressure of the patient and by causing the operation of the expiration circuit comprising the expiration valve 14 following through the proportional electro-valve 15 in which, in this configuration, the flow generator is connected to the second circuit, the non-return flap 12 of the first circuit 3 permitting preserving a pressure slightly greater in the second circuit relative to the first circuit. Thus, the device permits providing a respiratory gas according to respiratory cycles comprising phases of inspiration and expiration, the measuring means 5, 6, 7, 8 and the computation means 9 acting on the speed control means 10 to automatically control the speed of rotation of the turbine 2a as a function of the pressure and/or volume standards, of the detection of inspiration and expiration phases, of patient pressure signals and/or inspiration flow rate signals.

With the device of the invention, the expiration valve 14 is controlled by the pressure during the inspiration phase and by a regulating member during the expiration phase.

The device according to the invention thus, permits ventilating a patient by pressure or volume with a patient circuit provided with an expiration device controlled by a simple control of the speed of the turbine.

I claim:

1. A system for providing breathing assistance to a user, the system comprising:
   a housing;
   an exhalation valve interface coupled to or defined in the housing;
   a pressure control valve in fluid communication with the exhalation valve interface;
   an exhalation flow inlet coupled to or defined in the housing and defining a portion of an exhalation flow path; and
   a pressure sensor inside or coupled to the housing in pressure communication with the exhalation valve interface capable of generating a pressure signal;
   wherein the exhalation valve interface, the pressure control valve, and the pressure sensor are located along an exhalation valve control path, the exhalation valve control path being separate from the exhalation flow path such that exhaled gas flows through the exhalation flow path but not though the exhalation valve control path; and
   wherein the pressure sensor is located between the pressure control valve and an exhalation valve along the exhalation valve control path.

2. A system according to claim 1, further comprising a flow sensor in the housing in flow communication with the exhalation flow inlet, the flow sensor capable of generating a flow signal indicating a flow rate through the exhalation flow path.

3. A system according to claim 1, further comprising:
a blower inside or coupled to the housing;
a user inspiration flow outlet coupled to or defined in the housing and in flow communication with the blower; and
a flow sensor in the housing in flow communication with the exhalation flow inlet, the flow sensor capable of generating a flow signal indicating a flow rate through the exhalation flow path;
a second flow sensor inside or coupled to the housing in flow communication with the user inspiration flow outlet capable of generating a second flow signal;
a second pressure sensor inside or coupled to the housing in pressure communication with a proximal pressure interface capable of generating a second pressure signal;
a central processing unit in electrical communication with the pressure sensor, the second pressure sensor, the flow sensor, and the second flow sensor to receive pressure and flow signals therefrom; and
a blower speed controller in electrical communication with the central processing unit and the blower, wherein the central processing unit and the speed controller cooperate to control a speed of the blower based on at least two pressure and/or flow signals from any two or more of the pressure sensor, the second pressure sensor, the flow sensor, and the second flow sensor.

4. A system according to claim 3, wherein the central processing unit and the blower speed controller are adapted to transition from an inhalation phase to an exhalation phase during ventilation by deceleration of the blower.

5. A system according to claim 1, further comprising:
a blower inside or coupled to the housing;
a user inspiration flow outlet coupled to or defined in the housing and in flow communication with the blower; and
a proximal pressure interface coupled to or defined in the housing.

6. A system according to claim 5, further comprising at least one circuit connected to at least three of the user inspiration flow outlet, the exhalation valve interface, the proximal pressure interface, and the exhalation flow inlet.

7. A system according to claim 1, wherein the pressure control valve comprises an electro-valve located inside or coupled to the housing.

8. A system according to claim 7, wherein the electro-valve is in direct fluid communication with a blower.

9. A system according to claim 7, wherein the exhalation valve is arranged external to the housing and in fluid communication with the exhalation valve interface, the exhalation valve being controlled by gas pressure generated by a blower and further by the pressure control valve.

10. A system according to claim 1, further comprising:
a blower inside or coupled to the housing;
a user inspiration flow outlet coupled to or defined in the housing and in flow communication with the blower; and
a blower speed controller configured to control a speed of the blower.

11. A system for providing breathing assistance to a user, the system comprising:
a housing;
an exhalation valve control system defining an exhalation valve control path for controlling an exhalation valve external to the housing, the exhalation valve control system including a pressure control valve and a pressure sensor located between the pressure control valve and the exhalation valve along the exhalation valve control path; and
an exhalation flow conduit coupled to or defined in the housing and defining a portion of an exhalation flow path for communicating exhaled gas from the user;
wherein the exhalation valve control path is separate from the exhalation flow path such that exhaled gas flows through the exhalation flow path but not though the exhalation valve control path.

12. A system according to claim 11, further comprising:
an exhalation valve interface coupled to or defined in the housing and defining a portion of the exhalation valve control path; and
an exhalation flow inlet coupled to or defined in the housing and defining a portion of the exhalation flow path.

13. A system according to claim 12, further comprising:
a blower inside or coupled to the housing;
a user inspiration flow outlet coupled to or defined in the housing and in flow communication with the blower; and
a proximal pressure interface coupled to or defined in the housing.

14. A system according to claim 13, further comprising at least one circuit connected to at least three of the user inspiration flow outlet, the exhalation valve interface, the proximal pressure interface, and the exhalation flow inlet.

15. A system according to claim 11, wherein the exhalation valve control system further includes:
an exhalation valve interface coupled to or defined in the housing and defining a portion of the exhalation valve control path; and
wherein the pressure control valve comprises an electro-valve located inside or coupled to the housing.

16. A system according to claim 15, wherein the electro-valve is in direct fluid communication with a blower.

17. A system according to claim 15, wherein the exhalation valve is arranged external to the housing and in fluid communication with the exhalation valve interface, the exhalation valve being controlled by gas pressure generated by a blower and further by the pressure control valve.

18. A method for providing breathing assistance to a user, the method comprising:
measuring an exhalation flow in an exhalation flow path;
controlling a flow generator based at least on the measured exhalation flow;
measuring an exhalation valve control pressure in an exhalation valve control path at a location between a pressure control valve and an exhalation valve; and
controlling the exhalation valve by controlling the pressure control valve based at least on the measured exhalation valve control pressure;
wherein the exhalation valve control path is separate from the exhalation flow path such that exhaled gas flows through the exhalation flow path but not though the exhalation valve control path.

19. A system for providing breathing assistance to a user, the system comprising:
a gas supply system housing;
a patient circuit coupled between the gas supply system and the user;
an exhalation valve control system, including:
a exhalation valve control conduit;
a first valve coupled to the patient circuit and remote from the gas supply system; and a second valve within or coupled to the gas supply system housing, the second valve configured to control the first valve by controlling a pressure in the exhalation valve control conduit based on signals from a pressure sensor arranged between the first valve and the second valve; and an exhalation flow path for communicating exhaled gas from the user, the exhalation flow path separate from the exhalation valve control conduit such that exhaled gas flows through the exhalation flow path but not though the exhalation valve control conduit.

\* \* \* \* \*